US00PP27812P3

(12) United States Plant Patent
de Weert

(10) Patent No.: US PP27,812 P3
(45) Date of Patent: Mar. 28, 2017

(54) RASPBERRY PLANT NAMED 'ADVABEMAP'

(50) Latin Name: *Rubus idaeus*
Varietal Denomination: Advabemap

(71) Applicant: Gerrit de Weert, Rossum (NL)

(72) Inventor: Gerrit de Weert, Rossum (NL)

(73) Assignee: Advanced Berry Breeding, De Kwakel (NL)

( * ) Notice: Subject to any disclaimer, the term of this patent is extended or adjusted under 35 U.S.C. 154(b) by 68 days.

(21) Appl. No.: 14/544,824

(22) Filed: Feb. 24, 2015

(65) Prior Publication Data

US 2016/0249507 P1 Aug. 25, 2016

(51) Int. Cl.
*A01H 5/08* (2006.01)

(52) U.S. Cl.
USPC ..... Plt./204

(58) Field of Classification Search
USPC ..... Plt./156, 203, 204
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Raspberry plant named 'Advabemap', characterized by its upright and somewhat bushy plant habit; freely basal branching habit; high fruit production; uniform fruit ripening; large firm medium red-colored fruits; pleasant and sweet fruit taste; good fruit postharvest longevity; and fruits suitable for fresh consumption and processing.

3 Drawing Sheets

Botanical designation: *Rubus idaeus.*
Cultivar denomination: 'ADVABEMAP'.

BACKGROUND OF THE INVENTION

The present Invention relates to a new and distinct cultivar of Raspberry plant, botanically known as *Rubus idaeus* and hereinafter referred to by the name 'Advabemap'.

The new Raspberry plant is a product of a planned breeding program conducted by the Inventor in Rossum, Gelderland, The Netherlands. The objective of the breeding program was to develop new Raspberry plants with good fruit quality, productivity and uniformity.

The new Raspberry plant originated from a cross-pollination of two unidentified selections of *Rubus idaeus*, not patented. The new Raspberry plant was discovered and selected by the Inventor as a single plant from within the progeny of the stated cross-pollination in a controlled environment in Rossum, Gelderland, The Netherlands in September, 2008.

Asexual reproduction of the new Raspberry plant by root cuttings in a controlled environment at Rossum, Gelderland, The Netherlands since the spring of 2009 has shown that the unique features of this new Raspberry plant are stable and reproduced true to type in successive generations of asexual reproduction.

SUMMARY OF THE INVENTION

Plants of the new Raspberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Advabemap'. These characteristics in combination distinguish 'Advabemap' as a new and distinct Raspberry plant:

1. Upright and somewhat bushy plant habit.
2. Freely basal branching habit.
3. High fruit production.
4. Uniform fruit ripening.
5. Large firm medium red-colored fruits.
6. Pleasant and sweet fruit taste.
7. Good fruit postharvest longevity; fruits do not darken in color after harvesting.
8. Fruits are suitable for fresh consumption and processing.

Plants of the new Raspberry differ primarily from plants of the parent selections in the following characteristics:

1. Plants of the new Raspberry produce more fruits per plant than plants of the parent selections.
2. Fruits of plants of the new Raspberry do not darken in color after harvesting whereas fruits of plants of the parent selections darken in color after harvesting.

Plants of the new Raspberry can be compared to plants of *Rubus idaeus* 'Polka', not patented. In side-by-side comparisons conducted in Rossum, Gelderland, The Netherlands, plants of the new Raspberry differed from plants of 'Polka' in the following characteristics:

1. Plants of the new Raspberry were more freely basal branching than plants of 'Polka'.
2. Plants of the new Raspberry had thicker lateral branches with smaller thorns than plants of 'Polka'.
3. Fruits of plants of the new Raspberry were larger than fruits of plants of 'Polka'.
4. Fruits of plants of the new Raspberry did not darken in color after harvest whereas fruits of plants of 'Polka' darkened in color after harvest.
5. Plants of the new Raspberry produced more fruit per plant than plants of 'Polka'.

BRIEF DESCRIPTION OF THE PHOTOGRAPHS

The accompanying colored photographs illustrate the appearance of the new Raspberry plant showing the colors as true as it is reasonably possible to obtain in colored reproductions of this type. Colors in the photographs may differ slightly from the color values cited in the detailed botanical description which accurately describe the colors of the new Raspberry plant.

The photograph on the first sheet is a side perspective view of typical plants of 'Advabemap'.

The photograph on the second sheet is a close-up view of a typical plant of 'Advabemap' with developing fruits.

The photograph on the third sheet is a close-up view of typical fruits of 'Advabemap'.

DETAILED BOTANICAL DESCRIPTION

The aforementioned photographs, following observations and measurements describe plants grown during the summer and autumn in 30-liter containers in an outdoor nursery in De Kwakel, The Netherlands and under typical cultural practices of Raspberry plant production. During the production of the plants, day temperatures averaged 17° C. and night temperatures averaged 15° C. Plants were one year old when the photograph and description were taken. In the following description, color references are made to The Royal Horticultural Society Colour Chart, 1995 Edition, except where general terms of ordinary dictionary significance are used.

Botanical classification: *Rubus idaeus* 'Advabemap'.

Parentage:

*Female, or seed, parent*.—Unidentified selection of *Rubus idaeus*, not patented.

*Male, or pollen, parent*.—Unidentified selection of *Rubus idaeus*, not patented.

Propagation:

*Type*.—By root cuttings.

*Time to initiate roots, summer*.—About 12 to 14 days at temperatures about 15° C. to 17° C.

*Time to produce a rooted young plant, summer*.—About six weeks at temperatures about 15° C. to 17° C.

*Root description*.—Medium to thin in thickness, fibrous; brownish white in color.

*Rooting habit*.—Freely branching; dense.

Plant description:

*Plant and growth habit*.—Upright and somewhat bushy plant habit; vigorous growth habit; rapid growth rate.

*Plant height*.—About 2 meters.

*Plant diameter*.—About 50 cm.

Lateral branch description:

*Branching habit*.—Freely basal branching habit with about seven to eight basal branches developing per plant.

*Length*.—About 50 cm.

*Diameter*.—About 8 mm.

*Internode length*.—About 6 cm to 7 cm.

*Strength*.—Strong.

*Aspect*.—Mostly erect.

*Texture*.—Smooth, glabrous.

*Color, developing*.—Close to 176A.

*Color, developed*.—Close to 182B.

*Thorns*.—Density: About five per linear cm. Length: About 1 mm. Width: About 1 mm. Shape: Roughly deltoid. Apex: Acuminate. Base: Truncate. Margin: Entire. Color, immature: Close to 183B. Color, mature: Close to 183A.

Leaf description:

*Arrangement*.—Alternate; compound with typically three leaflets.

*Length, leaf*.—About 14 cm.

*Length, terminal leaflet*.—About 10 cm.

*Length, lateral leaflets*.—About 10 cm.

*Width, leaf*.—About 15 cm to 17 cm.

*Width, terminal leaflet*.—About 7 cm.

*Width, lateral leaflets*.—About 5 cm.

*Leaflet shape*.—Ovate.

*Leaflet apex*.—Cuspidate.

*Leaflet base*.—Cordate to cuneate.

*Leaflet margin*.—Double serrate.

*Leaflet texture, upper and lower surfaces*.—Slightly rippled, glabrous.

*Leaflet venation*.—Pinnate.

*Leaflet color*.—Developing leaflets, upper surface: Close to 144B. Developing leaflets, lower surface: Close to 194B. Fully expanded leaflets, upper surface: Close to 143B; venation, close to 144A. Fully expanded leaflets, lower surface: Close to 194B; venation, close to 147D.

*Petioles*.—Length, leaf: About 6 cm to 7 cm. Length, terminal leaflet: About 3 cm. Length, lateral leaflets: About 3 mm. Diameter, leaf: About 3 mm. Diameter, terminal leaflet: About 3 mm. Diameter, lateral leaflets: About 3 mm. Texture, upper and lower surfaces: Sparsely prickled. Color, upper and lower surfaces: Close to 145B.

Flower description:

*Flower form and flowering habit*.—Single star-shaped flowers arranged in axillary sprays; freely flowering with about four to six flowers per spray; flowers face mostly outwardly.

*Fragrance*.—None detected.

*Natural flowering season*.—Plants flower during the spring and autumn in The Netherlands.

*Flower buds*.—Length: About 5 mm to 10 mm. Diameter: About 5 mm to 10 mm. Shape: Roughly deltoid with acuminate apex. Color: Close to 141D.

*Flower diameter*.—About 2.5 cm.

*Flower depth (height)*.—About 7 mm.

*Petals*.—Arrangement: Single whorl of five petals. Length: About 1.5 cm. Width: About 3 mm to 5 mm. Shape: Lanceolate to narrowly ovate. Apex: Obtuse. Base: Attenuate. Margin: Entire. Texture, upper and lower surfaces: Smooth, glabrous. Color: When opening and fully opened, upper surface: Close to 155D. When opening and fully opened, lower surface: Close to 155D.

*Sepals*.—Arrangement: Single whorl of five sepals. Length: About 2 cm. Width, at the base: About 1 cm. Shape: Deltoid. Apex: Acuminate. Margin: Entire. Texture, upper and lower surfaces: Slightly pubescent. Color: When developing upper surface: Close to 145B. When developing, lower surface: Close to 139C. Fully developed, upper and lower surfaces: Close to 139D.

*Peduncles*.—Length: About 5 cm to 10 cm. Diameter: About 1.5 mm. Strength: Strong. Texture: Prickled. Color: Close to 145A.

*Pedicels*.—Length: About 3 cm to 5 cm. Diameter: About 1.5 mm. Strength: Strong. Texture: Prickled. Color: Close to 145B.

*Reproductive organs*.—Stamens: Quantity per flower: About 50 or more. Filament color: Close to 155D. Anther length: About 1 mm. Anther color: Close to 164C and 156C. Pollen color: Close to 196C. Pistils: Quantity per flower: About 50 or more. Stigma shape: Rounded. Stigma color: Close to 155D. Style length: About 5 mm. Style color: Close to 155D. Ovary color: Close to 155D. Receptacles: Height: About 1 cm. Diameter: About 1 cm. Shape: Conical. Color: Close to 155D. Fruits (aggregate of drupelets): Harvest season and productivity: Early to mid-season; plant produce harvestable fruits from the middle of August to the middle of October in Rossum, The Netherlands; plants of the new Raspberry produce 16,000 to 18,000 kg per hectare during the harvest season. Market use: Fruits suitable for fresh consumption and processing. Quantity: One per flower. Number of drupelets per fruit: About 100 or more. Length: About 3 cm. Diameter: About 2.3 cm to 2.5 cm. Shape: Broadly conical. Weight: About 5 to 7 grams. Firmness: Firm. Taste: Pleasant, sweet. Luster: Glossy. Postharvest longevity: Good postharvest longevity, fruits last for at least seven days at 2° C.; fruits do not darken in color after harvest. Color: Close to 45B. Seeds: Quantity: One per drupelet. Length: About 2.5 mm. Diameter: About 1 mm. Texture: Smooth, glabrous. Color: Close to 20D.

Disease & pest resistance: Plants of the new Raspberry have not been noted to be resistant to pathogens and pests common to Raspberry plants.

Temperature tolerance: Plants of the new Raspberry have been observed to tolerate temperatures ranging from 4° C. to 30° C.

It is claimed:

1. A new and distinct Raspberry plant named 'Advabemap' as illustrated and described.

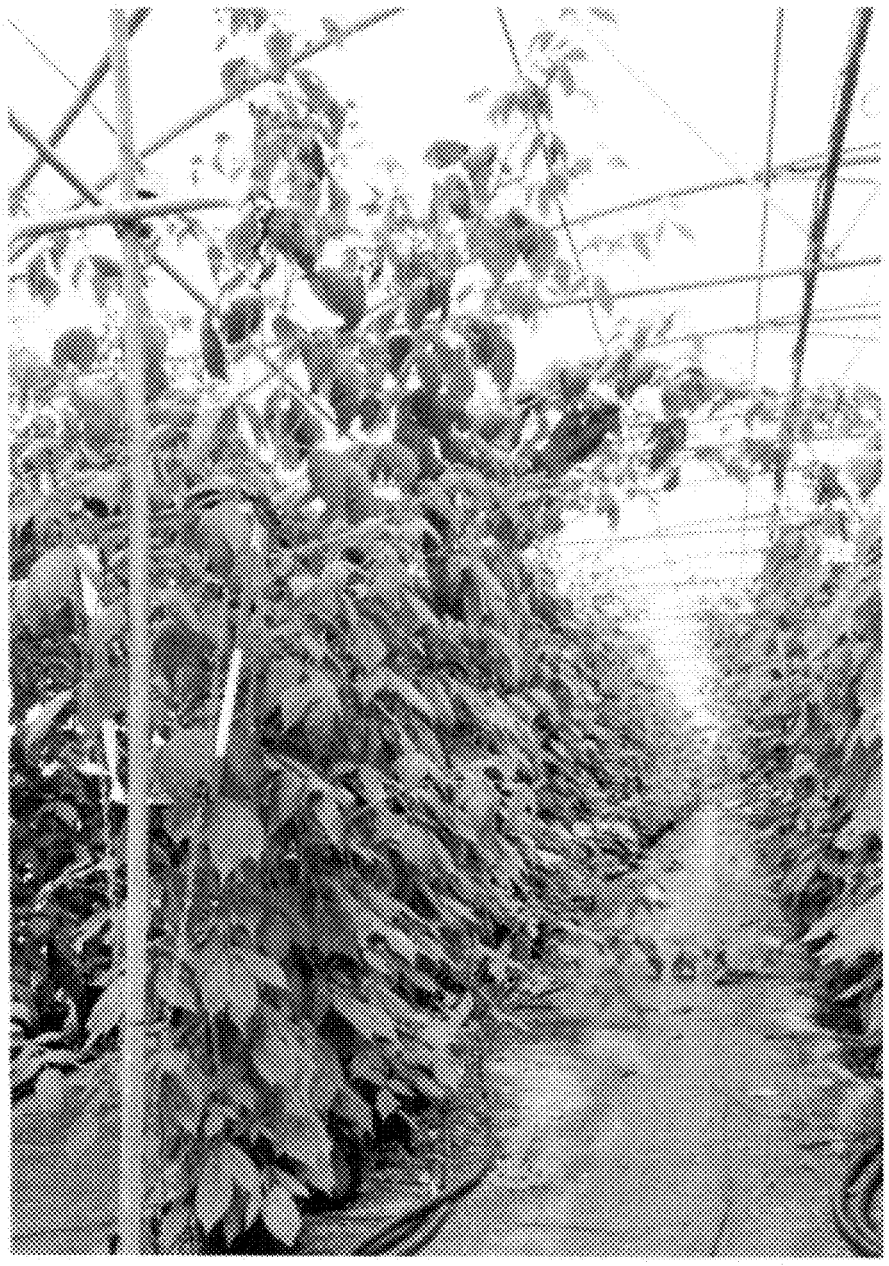

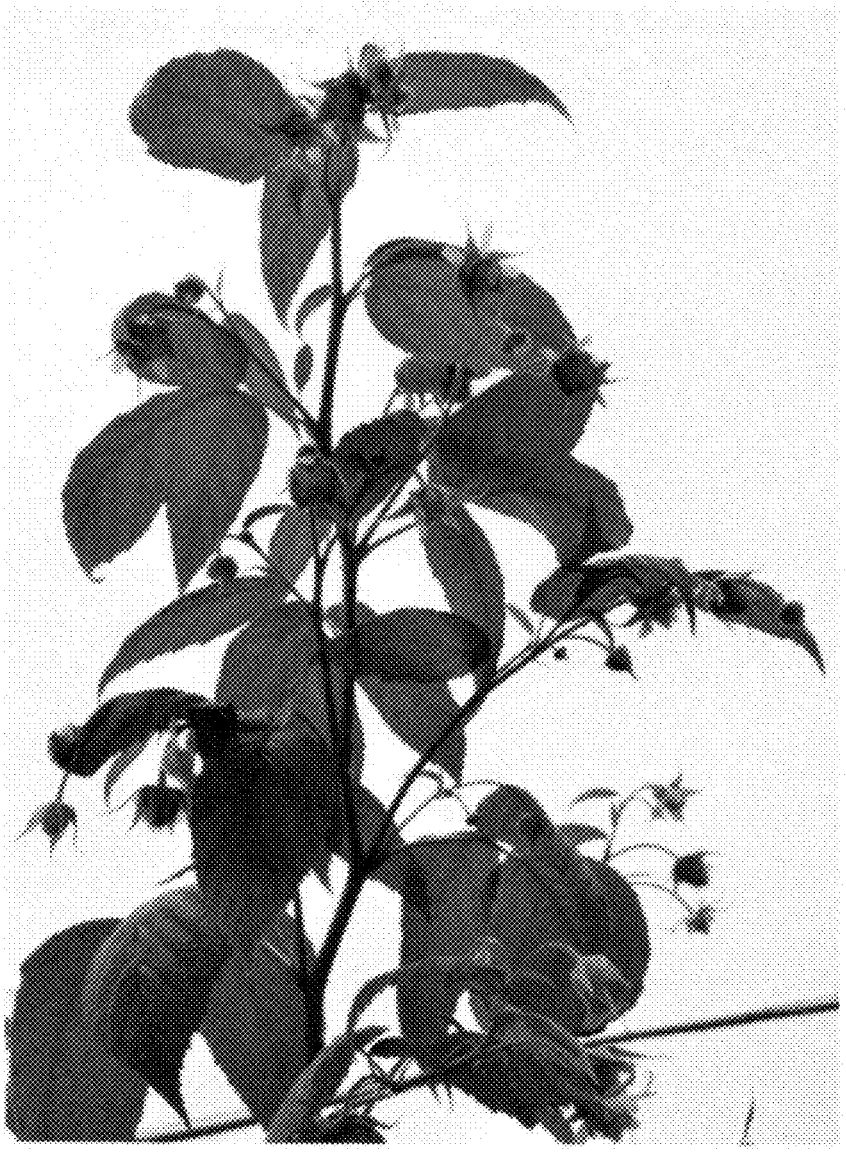

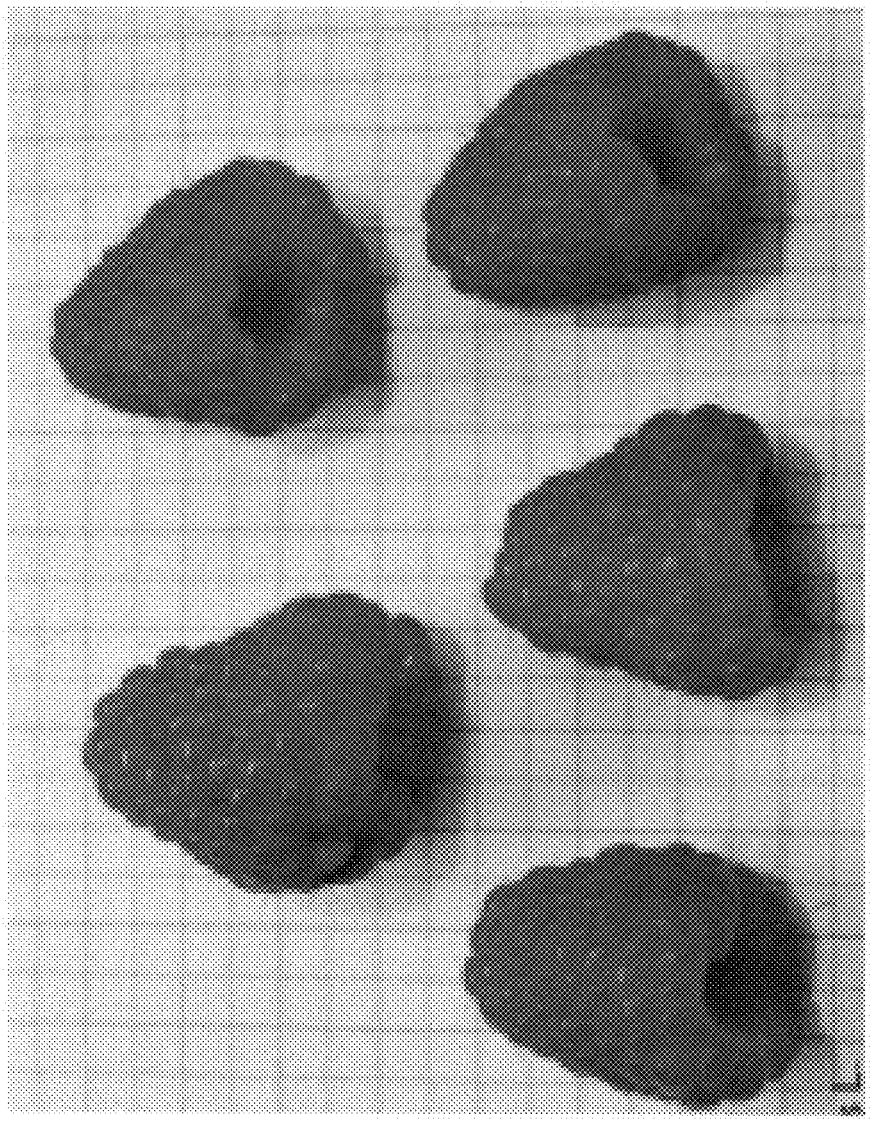

* * * * *